United States Patent
Kasahara

(10) Patent No.: US 6,659,610 B2
(45) Date of Patent: Dec. 9, 2003

(54) CORNEAL ENDOTHELIUM ANALYSIS SERVICE METHOD AND SYSTEM

(75) Inventor: Tatsuya Kasahara, Hyogo (JP)

(73) Assignee: Konan Medical, Inc., Hyogo (JP)

( * ) Notice: Subject to any disclaimer, the term of this patent is extended or adjusted under 35 U.S.C. 154(b) by 63 days.

(21) Appl. No.: 10/022,455

(22) Filed: Dec. 13, 2001

(65) Prior Publication Data

US 2002/0113942 A1 Aug. 22, 2002

(30) Foreign Application Priority Data

Dec. 27, 2000 (JP) ........................... 2000-397556

(51) Int. Cl.[7] .................................. A61B 3/14
(52) U.S. Cl. ........................................ 351/206
(58) Field of Search ................ 351/205, 206, 351/207, 211, 212; 705/3, 2; 128/898, 903, 904, 920, 922, 923, 924, 925

(56) References Cited

U.S. PATENT DOCUMENTS 5,471,261 A * 11/1995 Yoshizo et al. ............. 351/210
6,470,320 B1 * 10/2002 Hildebrand et al. ........... 705/3

FOREIGN PATENT DOCUMENTS

| JP | 02-000362 | 1/1990 |
|---|---|---|
| JP | 06-274600 | 9/1994 |
| JP | 07-000362 | 1/1995 |
| JP | 07-075624 | 3/1995 |
| JP | 08-243082 | 9/1996 |
| JP | 09-028682 | 2/1997 |
| JP | 09-311902 | 12/1997 |
| JP | 09-313442 | 12/1997 |
| JP | 10-43138 | 2/1998 |
| JP | 10-510187 | 10/1998 |
| WO | WO 96/17545 | 6/1996 |

* cited by examiner

Primary Examiner—George Manuel
(74) Attorney, Agent, or Firm—Marshall, Gerstein & Borun LLP

(57) ABSTRACT

A corneal endothelium analysis service method which provides an analysis service of corneal endothelium image data to a client through a network, includes a receiving step for receiving the corneal endothelium image data which is transmitted from a terminal owned by a client. The received corneal endothelium image data is analyzed and the analysis result is transmitted to the client terminal.

14 Claims, 11 Drawing Sheets

CORNEAL ENDOTHELIUM ANALYSIS SERVICE METHOD AND SYSTEM

BACKGROUND OF THE INVENTION

1. Field of the Invention

The present invention relates to a corneal endothelium analysis service method and system for providing analysis results of image data of corneal endothelium to clients through a computer network.

2. Description of the Related Art

In recent years, the number of persons wearing contact lenses has been rapidly increasing. Since the corneal endothelium of these persons might be damaged because of the long-term use of the contact lenses, they must have corneal endothelium examined on a regular basis.

Conventionally, for such examination of the corneal endothelium, a set of a corneal endothelium photographing device for photographing the corneal endothelium and a corneal endothelium analysis device for analyzing the image data of the corneal endothelium photographed by the photographing device and calculating various evaluation values. The set of these devices are installed at contact lens shops, glass shops, hospitals, clinics, etc.

The corneal endothelium photographing device is disclosed in Japanese Laid-Open Patent Publications Nos. 7-75624, 2-362, or the like. In general, the corneal endothelium photographing device comprises a photographing portion including various optical systems such as an anterior segment observing optical system, a photographing optical system, an alignment optical system, and a focusing optical system, a photographing portion drive mechanism for driving the photographing portion to be moved in X, Y, and Z directions, a control portion for controlling the photographing portion drive mechanism for alignment and focusing, or the like. The corneal endothelium photographing device capable of photographing the corneal endothelium automatically or semiautomatically has been commercially available.

Examples of the corneal endothelium analysis device are a manual analysis device that requires processing by an operator and an automatic analysis device that performs image processing. In these devices, based on image data of the corneal endothelium sent from the corneal endothelium photographing device, various evaluation values including an average cell area of the corneal endothelium, the number of corneal endothelium cells per unit area, standard deviation of corneal endothelium cell areas, a variation coefficient of the corneal endothelium cell areas, the rate of appearance of a hexagon cell, etc are analyzed.

While the corneal endothelium analysis device by the manual analysis is inexpensive, large amount of labor of the operator and time are required. Besides, since the operator might make mistakes in judgment or entering data, the accuracy of the analysis is low.

On the other hand, the large amount of labor of the operator is unnecessary and therefore, no mistakes are made in the corneal endothelium analysis device by the automatic analysis, but the device is very expensive, so that many users do not enjoy the convenience of the device.

SUMMARY OF THE INVENTION

The present invention has been developed for solving the above-described problem, and an object of the present invention is to provide a corneal endothelium analysis service method and system capable of providing accurate analysis results of corneal endothelium to a client who needs analysis of the corneal endothelium at a low cost without a need for a corneal endothelium analysis device that increases operation burden and is expensive.

According to the present invention, there is provided a corneal endothelium analysis service method which provides an analysis service of corneal endothelium image data to a client through a network, comprising: a receiving step for receiving the corneal endothelium image data which is transmitted from a terminal owned by a client (client terminal); an analyzing step for analyzing the received corneal endothelium image data; and a first transmission step for transmitting an analysis result to the terminal.

In the corneal endothelium analysis service method, a client who needs analysis of the corneal endothelium transmits image data of an image of the corneal endothelium photographed by a corneal endothelium photographing device owned by the client through the network. The image data is received in the receiving step. The image data is analyzed in the analyzing step. The analysis result is transmitted in the first transmission step. With these steps, the analysis service of the corneal endothelium is provided to the client, and the client can quickly obtain the analysis result of the image data through the network. What is prepared by the client is only the corneal endothelium photographing device for analysis of the corneal endothelium. The method of the present invention need not a burdensome and expensive corneal endothelium analysis device that has been conventionally necessary for analysis of the corneal endothelium, and is therefore economical. Since at least one corneal endothelium analysis device prepared by a provider of the corneal endothelium analysis service method is satisfactory, it is not necessary to prepare the device for each client. Consequently, usage efficiency is increased as a whole. Further, by upgrading an analysis software used in the analysis step of the analysis service method of the corneal endothelium to the most up-to-date software, the client can always obtain the analysis result obtained by the newest analysis.

In the corneal endothelium analysis service method, the image data and items to be analyzed that are demanded by the client may be received in the receiving step, and only the items demanded by the client may be analyzed in the analyzing step. This is adaptable to how the client utilizes the corneal endothelium analysis service and only the items demanded by the client can be provided to the client at a reasonably low cost.

In the corneal endothelium analysis service method, the items analyzed in the analyzing step may include at least one item selected from a group comprising a processed corneal endothelium image, a minimum cell area of the corneal endothelium, a maximum cell area of the corneal endothelium, the number of analyzed corneal endothelium cells, an average cell area of the corneal endothelium, the number of corneal endothelium cells per unit area, standard deviation of corneal endothelium cell areas, a variation coefficient of the corneal endothelium cell areas and a rate of appearance of a hexagonal cell.

These items prepared in the analyzing step are satisfactory for examination of the corneal endothelium at the contact lens shops, the glass shops, the oculist, or the like.

The corneal endothelium analysis service method may further comprise: a storing step for storing analysis results and the image data as being associated with a subject; and a second transmission step for transmitting the stored analysis results in reply to a request from the client. The analysis results and the image data are stored as being associated with the subject in the storing step, and the stored analysis results are transmitted in the second transmission step. Therefore, the client can observe time-series analysis results of the corneal endothelium for each subject easily and quickly and obtain more accurate analysis results.

The corneal endothelium analysis service method, may further comprise: a photographing step for controlling a photographing operation of a corneal endothelium photographing device owned by the client and photographing the corneal endothelium of a subject via the network and the client terminal. Thereby, a photographing operation (e.g. alignment, focusing) of the corneal endothelium photographing device owned by the client is directly controlled in the photographing step via the network and the client terminal, and under the control, the corneal endothelium of the subject can be photographed. Therefore, the photographing step simplifies an operation of an operator on the side of the client, and hence eliminates the need for the operator.

The corneal endothelium analysis service method may further comprise: an instructing step for observing a condition of the subject with respect to the corneal endothelium photographing device and transmitting an instruction to the terminal to bring the subject into a condition under which the subject can be photographed via the network and the terminal. The instructing step allows the subject to easily take an appropriate attitude for photographing. Therefore, the instructing step further simplifies the operation of the operator on the side of the client, and hence further eliminates the need for the operator.

The corneal endothelium analysis service method, may further comprise: a calculating step for calculating fee of the analysis service; and an accounting step for performing accounting of the calculated fee to the client. In the calculating step and the accounting step, accounting of appropriate fee to the client can be quickly performed, and the client can enjoy the analysis service of the demanded items of the corneal endothelium at a low cost.

In the corneal endothelium analysis service method, each of the steps (receiving step, analyzing step, first transmission step, storing step, second transmission step, photographing step, instructing step, calculating step, and accounting step) may be performed by using a site on Internet. These days, since the Internet is widely used, everybody can enjoy the corneal endothelium analysis service easily and quickly.

In the corneal endothelium analysis service method, each of the steps may be performed under control of the client terminal accessing the site. Since the corneal endothelium image data and image-processed corneal endothelium image data have large amount of information, relatively much time is required in transmission/reception via the network. So, by downloading the program for executing the analyzing step or the like to the client terminal accessing the site and executing each of the steps under control of the client terminal, transmission of the image data becomes unnecessary and the analysis service of the corneal endothelium can be provided at real time.

According to the present invention, there is also provided a corneal endothelium analysis service system which provides an analysis service of corneal endothelium image data to a client through a network, comprising: a receiving means for receiving the corneal endothelium image data which is transmitted from a terminal owned by a client; an analyzing means for analyzing the received corneal endothelium image data; and a first transmission means for transmitting an analysis result to the terminal.

In the corneal endothelium analysis service system, similarly to the corneal endothelium analysis service method, what is prepared by the client is only the corneal endothelium photographing device for analysis of the corneal endothelium. The service system of the present invention need not a burdensome and expensive corneal endothelium analysis device that has been conventionally necessary for analysis of the corneal endothelium. Simultaneously, everybody can enjoy the analysis service of the corneal endothelium that is highly accurate and effective at a low cost.

Similarly to the method, in the corneal endothelium analysis service system, the image data and items to be analyzed that are demanded by the client may be received by the receiving means, and only the items demanded by the client may be analyzed by the analyzing means. The items analyzed by the analyzing means may include at least one item selected from a group comprising a processed corneal endothelium image, a minimum cell area of the corneal endothelium, a maximum cell area of the corneal endothelium, the number of analyzed corneal endothelium cells, an average cell area of the corneal endothelium, the number of corneal endothelium cells per unit area, standard deviation of corneal-endothelium cell areas, a variation coefficient of the corneal endothelium cell areas and a rate of appearance of a hexagonal cell. The corneal endothelium analysis service system may further comprise: a storing means for storing analysis results and the image data as being associated with the subject; a second transmission means for transmitting the stored analysis results in reply to a request from the client; a photographing means for controlling a photographing operation of a corneal endothelium photographing device owned by the client and photographing the corneal endothelium of the subject via the network and the terminal; an instructing means for observing a condition of the subject with respect to the corneal endothelium photographing device and transmitting an instruction to the terminal to bring the subject into a condition under which the subject can be photographed via the network and the terminal; a calculating means for calculating fee of the analysis service; and an accounting means for performing accounting of the calculated fee to the client. In the corneal endothelium analysis service system, each of the means may be performed by using a site on Internet and each of the means may be performed under control of the terminal accessing the site.

The above and further objects and features of the invention will more fully be apparent from the following detailed description with reference to accompanying drawings.

DETAILED DESCRIPTION OF THE PREFERRED EMBODIMENTS

Figure 1:
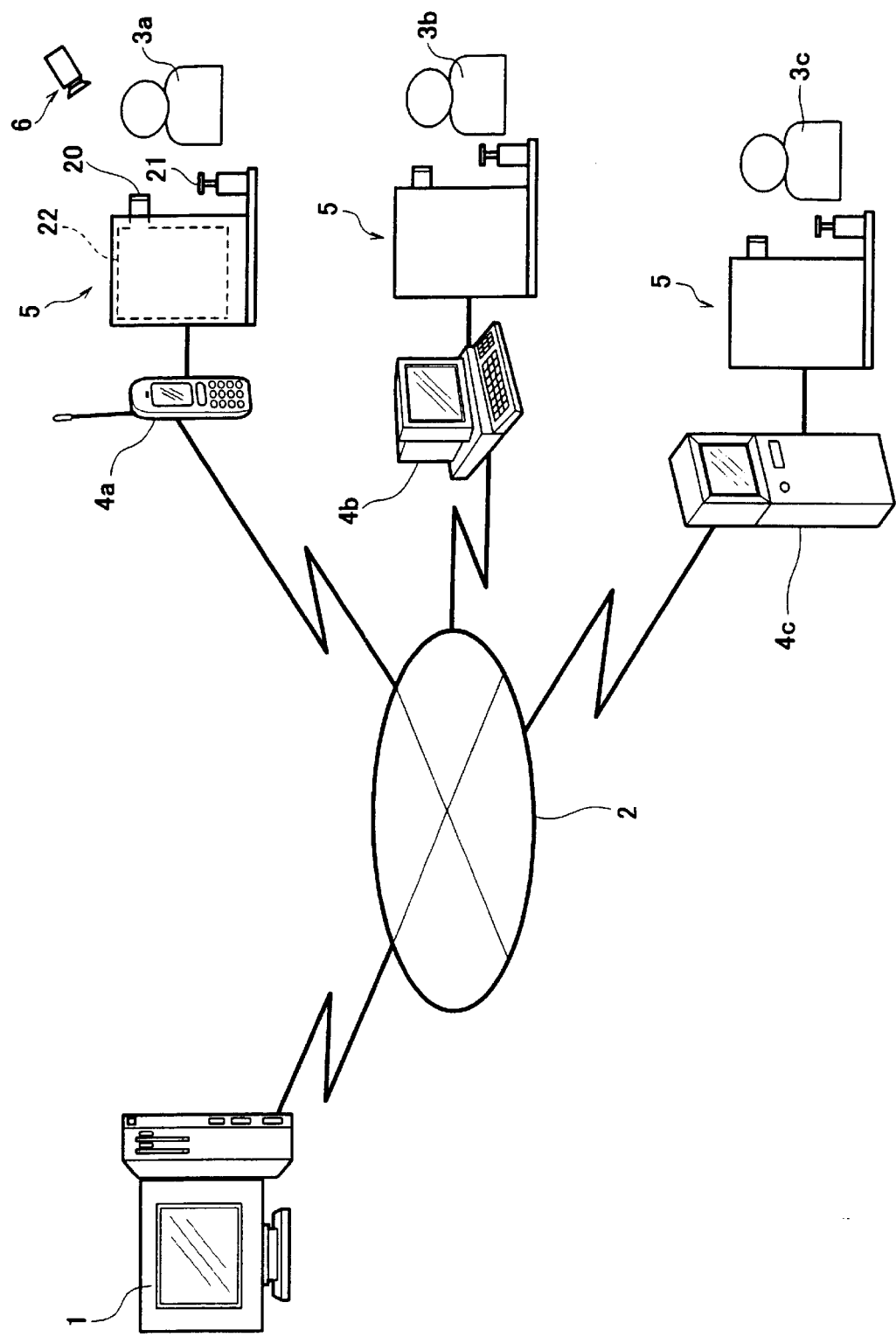
FIG. 1 is a block diagram showing a configuration of a corneal endothelium analysis service system according to an embodiment of the present invention.
Figure 2:
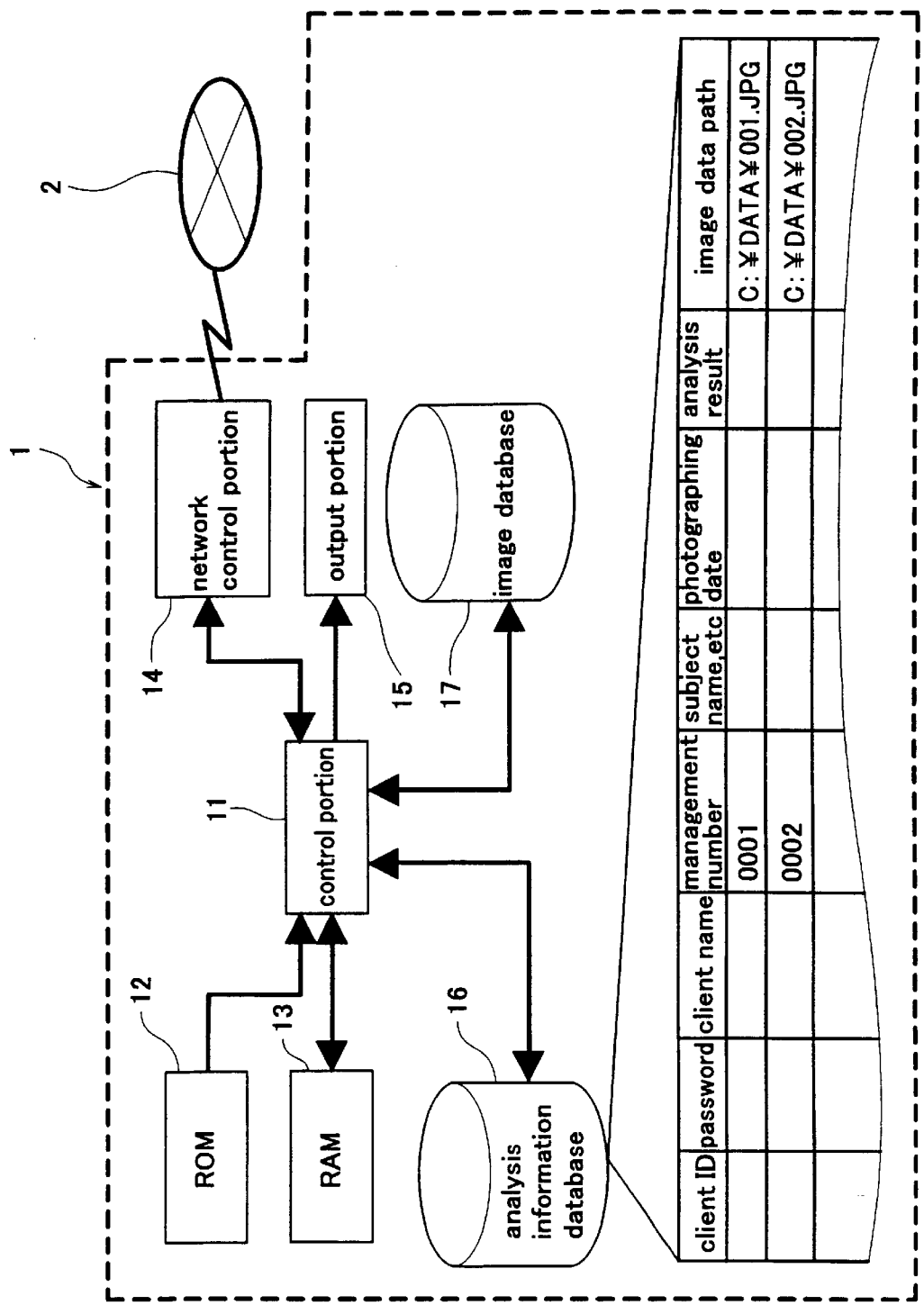
FIG. 2 is a block diagram showing a configuration of a server of the corneal endothelium analysis service system of FIG. 1.

Hereinafter, preferred embodiments of the present invention will be described with reference to drawings. FIG. 1 is a block diagram showing a configuration of a corneal endothelium analysis service system according to an embodiment of the present invention. FIG. 2 is a block diagram showing a configuration of a server of the corneal endothelium analysis service system of FIG. 1. FIGS. 3–6 are flowcharts each showing a procedure of the corneal endothelium analysis service system of FIG. 1 based on communication between the server and the client terminal. FIGS. 7–11 are views each showing an example of an image display of a site on Internet that executes the corneal endothelium analysis service system of FIG. 1.

Referring now to FIG. 1, the corneal endothelium analysis service system of FIG. 1 is comprised of a server (server machine) 1 connected to a network 2 and capable of doing business that provides an analysis service of corneal endothelium to a plurality of clients 3 (3a, 3b, 3c) through the network 2. The operation of server 1 may be directly performed by a provider of the corneal endothelium analysis service or by an entrusted agent.

The plurality of clients 3a, 3b, 3c who utilize the corneal endothelium analysis service system can connect client terminals 4a, 4b, 4c, as various communication devices respectively owned by the clients to the network 2. In FIG. 1, the client terminal 4a is represented by a cellular phone (net cellular phone), the client terminal 4b is represented by a personal computer, and a client terminal 4c is represented by an interactive kiosk installed at a shop such as contact lens shop. The client terminals 4a, 4b, 4c respectively have analog-to-digital conversion circuits (not shown). The analog-to-digital conversion circuits respectively allow images of corneal endothelium photographed by corneal endothelium photographing devices 5 (mentioned later) owned by the clients 3a, 3b, 3c to be converted into digital image data, which are sent from the client terminals 4a, 4b, 4c to the network 2 according to operations of the clients 3a, 3b, 3c.

The network 2 is capable of performing communication of the image data according to configurations of the client terminals 4a, 4b, 4c. The network 2 may be the combination of plural types of networks when the client terminals 4a, 4b, 4c are configured in various ways. Specifically, in case of the cellular phone (client terminal 4a), the network 2 is generally a web data communication network for the cellular phone managed by a cellular phone communication agency. The "cellular phone" refers to a cellular phone in a broad sense and includes a PHS (Personal Handyphone System) and the like advantageous in data communication, or otherwise, this may be replaced by a PDA (Personal Digital Assignment) or the like. In case of a personal computer (client terminal 4b), the network 2 is generally Internet/Intranet. Further, in case of the interactive kiosk (client terminal 4c), the network 2 is a dedicated network utilizing satellite communication managed by various groups comprising contact lens shops or the like.

The server 1 configured as the corneal endothelium analysis service system, the clients 3 each having the client terminal 4 and the corneal endothelium photographing device 5, and the network 2 connecting the server 1 and the client terminal 4 provide an analysis service business of the corneal endothelium.

Subsequently, the configuration of the sever 1 will be explained in detail. Referring to FIG. 2, the server 1 comprises a control portion 11, a ROM 12, a RAM 13, a network control portion 14, an output portion 15, an analysis information database 16, and an image database 17.

The control portion 11 is comprised of a CPU or the like and serves to control respective portions of the server 1 according to a computer program stored in the ROM 12. The ROM 12 contains the computer program needed by the server 1 for executing the corneal endothelium analysis service method according to the present invention. The RAM 13 serves to store temporary data generated during an operation of the control portion 11. The network control portion 14 is an interface enabling the communication performed by the control portion 11 via the above-described various networks 2. The output portion 15 comprises various displays such as a CRT (Cathode Ray Tube) display, a LCD (Liquid Crystal Display) or the like, and an electrophotgraphic printer or the like.

The analysis information database 16 is a database that stores information relating to analysis of the corneal endothelium analyzed in reply to a request from the client 3 (representing the clients 3a, 3b, 3c) as being associated with a subject. The analysis information database 16 contains attributes such as client IDs, passwords, client names, management numbers, subject names, photographing dates, various types of analysis results including an average cell area, image data path, or the like, and serves to store analysis information of one analysis as one record. In brief, the analysis information database 16 is a database used for managing the analysis requests from the client 3 and analysis results on the server 1 and may contain attributes other than the above items.

The client ID is a combination of characters assigned to the client 3. The password is a combination of characters associated with the client ID. The password, together with the client ID, is used for authentication of the client 3 by the server 1. The client name is a name of the client 3. The management number is a management number (lot number, etc) assigned according to the analysis request, and four-digit serial number is adopted herein. The subject name, etc., is used for identifying the subject associated with the analysis request from the client 3 and composed of the subject name and management numbers and symbols assigned to the subject. The photographing date indicates a photographing date of the corneal endothelium in reply to the analysis request. The various types of analysis results represent various evaluation values resulting from analysis of the corneal endothelium conducted in reply to the analysis request from the client. The image data path represents a storage area in the image database 17 in which the image data of the corneal endothelium associated with the analysis request is stored by a file name including the corresponding path.

The image database 17 is a database in which information of each management number of the analysis information database 16 and the corresponding corneal endothelium image data are stored. While the analysis information database 16 and the image database 17 are directly connected to the server 1 of FIG. 1, these databases may be connected via a suitable network such as LAN.

The corneal endothelium photographing device 5 owned by the client 3 is a known device disclosed in the above-described Japanese Laid-Open Patent Publications. In general, as shown in FIG. 1, the photographing device 5 is mainly composed of a vertically movable chin table 21 on which a chin of the subject is placed so that the subject's eyes to be tested (hereinafter simply referred to as eyes) conform to a photographing window 20, a photographing portion 22 for photographing the corneal endothelium of the eyes conforming to the photographing window 20, a photographing portion drive mechanism (not shown) for driving the photographing portion 22 to be movable in X, Y, and Z directions, a control portion (not shown) for controlling the photographing portion drive mechanism for alignment and focusing. The photographing portion 22 comprises a photographing optical system including a CCD (charged coupled device) camera or the like, for photographing the corneal endothelium, an alignment optical system for alignment, a focusing optical system for focusing, an anterior segment observing system for positioning of the eyes with respect to the photographing window 20, or the like. As described later, when the server 1 comprises photographing means for controlling a photographing operation of the corneal endothelium photographing device 5 of the client via the network 2, the control portion is unnecessary in the corneal endothelium photographing device 5.

The sever 1 comprises receiving means for receiving the image data of the corneal endothelium transmitted from the client terminal 4 by the client 3, analyzing means for analyzing the received corneal endothelium image data, and first transmission means for transmitting the analysis result to the client terminal 4 as basic means by activation of the control portion 11 according to the computer program stored in the ROM 12. According to the corneal endothelium analysis service system, the client 3 requiring analysis of the corneal endothelium is capable of transmitting the image data of the corneal endothelium photographed by the corneal endothelium photographing device 5 via the network 2, and quickly obtaining the analysis result of the image data via the network 2 from the server 1 at which the receiving means, the analyzing means, and the first transmission means are activated by the control portion 11 or the like, without a need for an expensive corneal endothelium analysis device.

The receiving means can receive items to be analyzed which are demanded by the client 3 as well as the image data and the analyzing means can analyze only the items. This is adaptable to how the corneal endothelium analysis service is utilized by the client 3, and provides only the items demanded by the client 3 at a low cost. The items to be analyzed include at least one selected from a processed corneal endothelium image, a minimum cell area of the corneal endothelium, and a maximum cell area of the corneal endothelium, the number of analyzed corneal endothelium cells, an average cell area of the corneal endothelium, the number of corneal endothelium cells per unit area, standard deviation of the corneal endothelium cell areas, a variation coefficient of the corneal endothelium cell areas, the rate of appearance the hexagon cell, and so forth, which are needed for examination of the corneal endothelium at the contact lens shops, the glass shops, oculist, or the like. For example, the following three patterns may be selected: (1) only the number of corneal endothelium cells per unit area as an essential item, (2) the number of corneal endothelium cells per unit area, the variation coefficient of the corneal endothelium cell area, and the rate of the hexagon cell as basic items, and (3) all the above items as full items. The processed corneal endothelium image refers to an output image obtained by subjecting an input entire image to image processing such as conversion, enhancement, reconstruction. Such image processing is included in the analysis of the corneal endothelium.

The server 1 further comprises storing means for storing the analysis results and the image data in the analysis information database 16 and the image database 17 as being associated with the subject and second transmission means for transmitting the analysis results stored in the analysis information database 16 as desired by the client 3. The storing means and the second transmission means allow the client 3 to easily obtain time-series analysis results of the corneal endothelium for each subject.

The server 1 further comprises photographing means for controlling a photographing operation (alignment, focusing, or the like) of the corneal endothelium photographing device 5 owned by the client 3 and photographing the corneal endothelium of the subject via the network 2 and the client terminal 4, instructing means for observing a condition of the subject with respect to the corneal endothelium photographing device 5 by using the photographing device 6 (e.g., CCD camera), the anterior segment observing optical system of the photographing portion 22 of the corneal endothelium photographing device 5, or the like, which are installed on the side of the client 3, and transmitting an instruction for instructing the subject to be into a condition under which the subject can be photographed, to the client terminal 4, and calculating means for calculating fee of the analysis service and accounting means for performing accounting of the calculated fee to the client.

The photographing means simplifies an operation of an operator on the side of the client 3, and hence eliminates the need for the operator. The instructing means enables the subject to have an appropriate attitude for photographing. Hence, the a instructing means further simplifies the operation of the operator on the client side and further eliminates the need for the operator. The calculating means and the accounting means enable quick accounting of the appropriate fee to the client 3.

By the use of the site on Internet for each means of the server 1, the corneal endothelium analysis service is easily and speedily available to everybody. Also, in the use of the site on Internet, each means can be executed under control of the client terminal 4 accessing the site. Thereby, the transmission of the image data via the network 2 becomes unnecessary, and consequently, the corneal endothelium analysis service can be provided in real time.

Subsequently, the flow of the process in which the server 1 analyzes the corneal endothelium image in reply to an analysis request from the client 3 will be explained with reference to FIGS. 3–11.

First, the client terminal 4 specifies a predetermined URL (Universal Resource Locator) (Step S1), thereby accessing the site being published on Internet (network 2) by the server 1. The data of such site can be prestored in the RAM 13.

Figure 7:
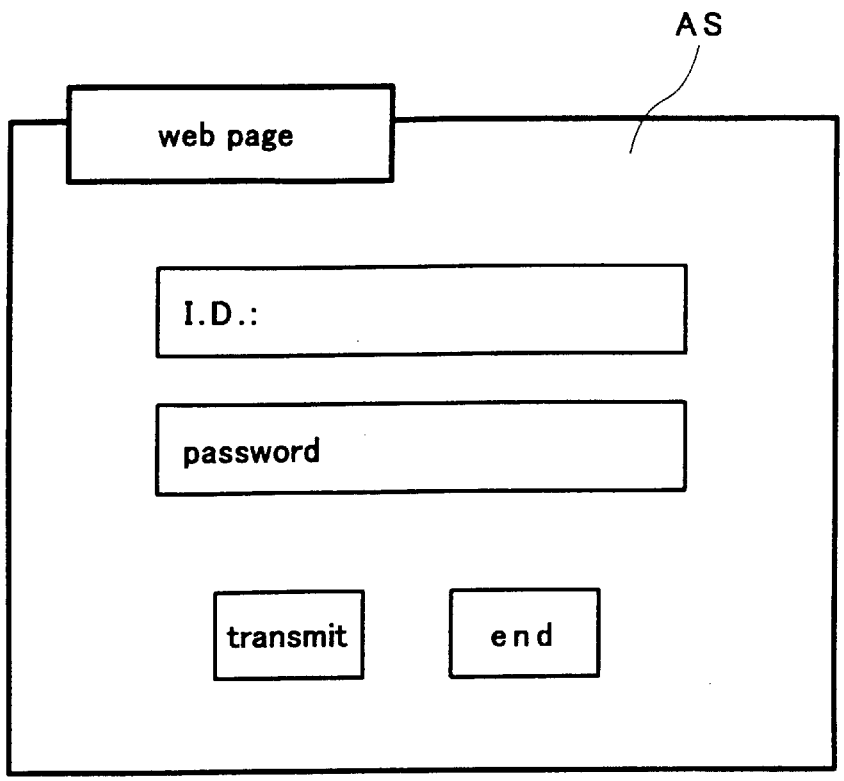
FIG. 7 is a view showing an example of an image display of a site on Internet that executes the corneal endothelium analysis service system of FIG. 1.

In accordance with the specification of the URL, the server 1 transmits a web page for authentification of the client 3 to the client terminal 4 (Step S2). The web page for user authentification is, as shown in FIG. 7, to request the client 3 to enter the ID and the password into entering portions provided therein. It should be noted that the subject information may be entered to the web page.

Upon receipt of the web page, the web page is displayed on a display portion of the client terminal 4 (Step S3). The client 3 enters the client ID and the password assigned to the client 3 to the entering portions (Step S4) and transmits them to the server 1 (Step S5).

The client ID and the password are transmitted and received by the server 1 (Step S6). The server 1 refers to the record of the ID in the analysis information database 16 to authenticate the client 3 by client authentification means that judges whether or not there is a match between the password described in the record and the entered password or the like (Step S7). When a fee is prepaid by the client 3 before providing the analysis service, the balance of the client 3 is checked in Step S7. When "pay in advance" is desired, accounting may be conducted at this time.

When the client 3 is not authenticated, the server 1 transmits an instruction for requesting the client 3 to re-enter the ID and the password to the client terminal 4 (Step S8), and at the client terminal 4, processing goes back to Step S4.

Figure 8:
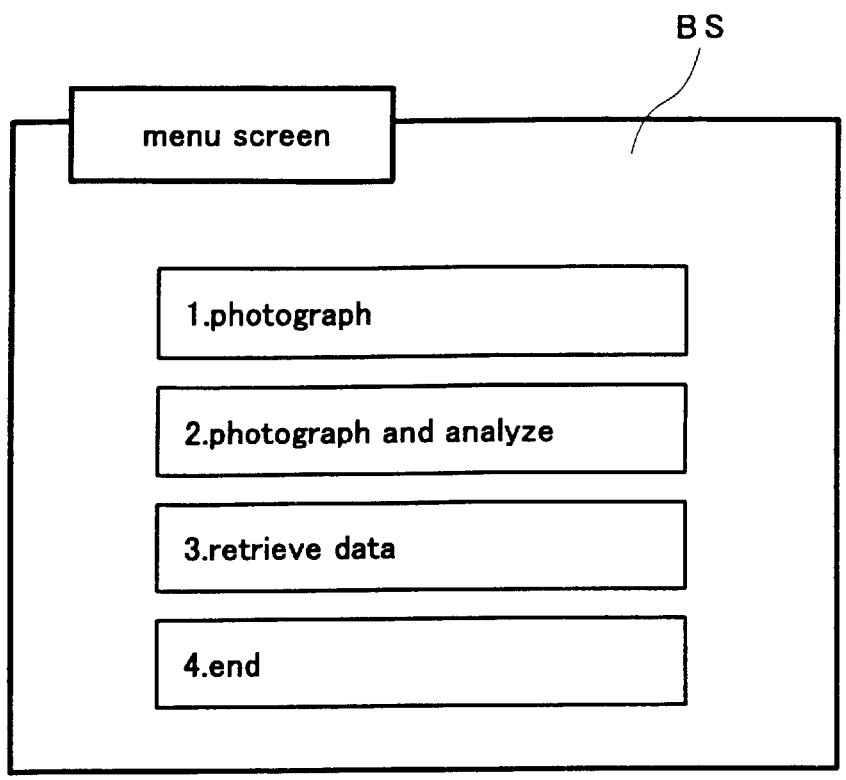
FIG. 8 is a view showing another example of the image display of the site on Internet that executes the corneal endothelium analysis service system of FIG. 1.
Figure 9:
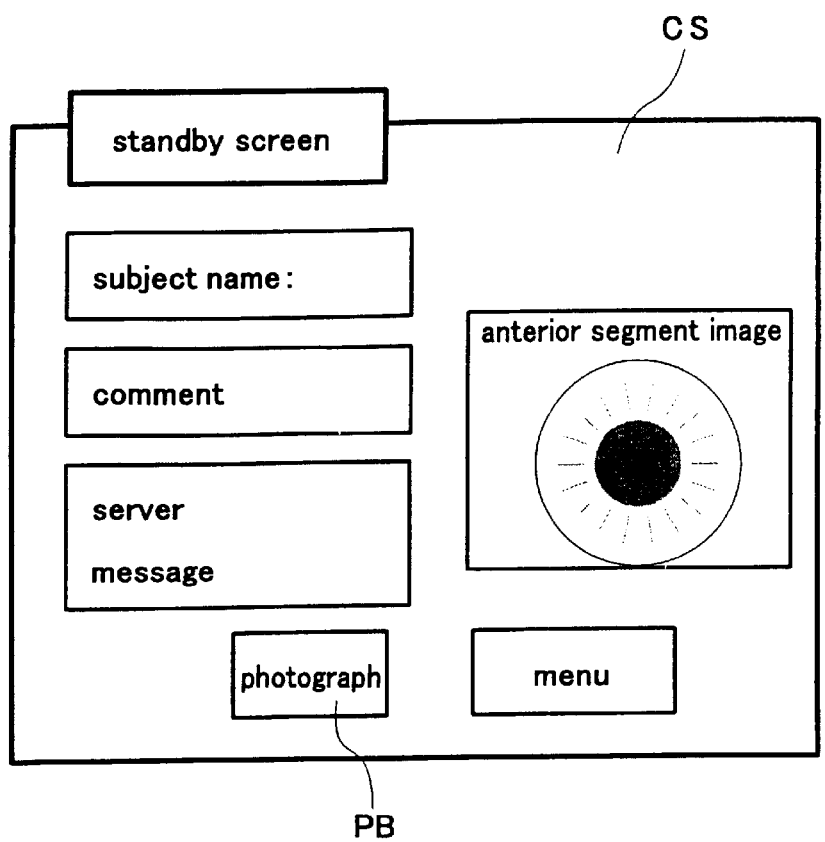
FIG. 9 is a view showing still another example of the image display of the site on Internet that executes the corneal endothelium analysis service system of FIG. 1.

On the other hand, when the client 3 has been authenticated, the server 1 transmits a permission to use the corneal endothelium photographing device 5 (Step S9), thereby making a menu screen BS displayed at the client terminal 4 as shown in FIG. 8. In this menu screen BS, the client 3 selects a desired service from "only photographing", "photographing and analysis", and "data retrieval" (Step S10). The "data retrieval" is to extract past comments describing illness history of the subject, past corneal endothelium image data of the subject, past analysis results of the subject, etc, for each subject. The "photographing" is to photograph the corneal endothelium. The "photographing and analysis" is to photograph the corneal endothelium and analyze the photographed corneal endothelium. The photographing, and photographing and analysis may be conducted along with the data retrieval as mentioned below and the items to be analyzed can be selected by the client 3. A case where the data retrieval is selected (Step S12) will be described later (FIG. 7). When the "photographing" or the "photographing and analysis" is selected (Step S11), a standby screen CS is displayed at the client terminal 4 as shown in FIG. 9.

Meanwhile, the respective optical systems (photographing optical system, alignment optical system, focusing optical system, anterior segment observing optical system) of the corneal endothelium photographing device 5 of the client 3, and the photographing device 6 for photographing the condition of the subject with respect to the corneal endothelium photographing device 5 are activated. A server message is displayed on the standby screen CS. For example, the message prompts the client 3 or the like to enter required items and guides the subject to look into the photographing window 20 (objective lens) of the corneal endothelium photographing device 5 and fix the eyes on a fixation target lamp for positioning of the eyes with respect to the photographing window 20 at the completion of entering. Or otherwise, the message is given through a speaker of the client terminal 4 in the form of a synthesized voice.

In accordance with such guiding instructions, the client 3 (or subject) enters subject information such comments relating to the subject such as a subject name, birthday of the subject, illness history of the subject, or the like, to the standby screen CS (Step S13). Then, the subject looks into the photographing window 20 and fixes the eyes on the fixation target lamp (Step S14). The condition of the subject with respect to the corneal endothelium photographing device 5, i.e., the condition of the subject photographed by the photographing device 5, and an image of anterior segment photographed by the anterior segment observing system, are transmitted to the server 1 (Step S15). The anterior segment image is displayed on the standby screen CS.

At the server 1, it is judged whether or not the subject can be photographed, that is, alignment will be possible, based on the transmitted subject condition (Step S16). When it is judged that the subject cannot be photographed, instructions or advices for guiding the subject to an appropriate condition are transmitted to the client terminal 4 (Step S17). The instructions or advices are given in the form of the synthesized voice through the speaker of the client terminal 4 or displayed on the display screen of the client terminal 4. Therefore, the subject performs Step S14 again. The steps S15–S17 correspond to the instructing Steps.

Figure 6:
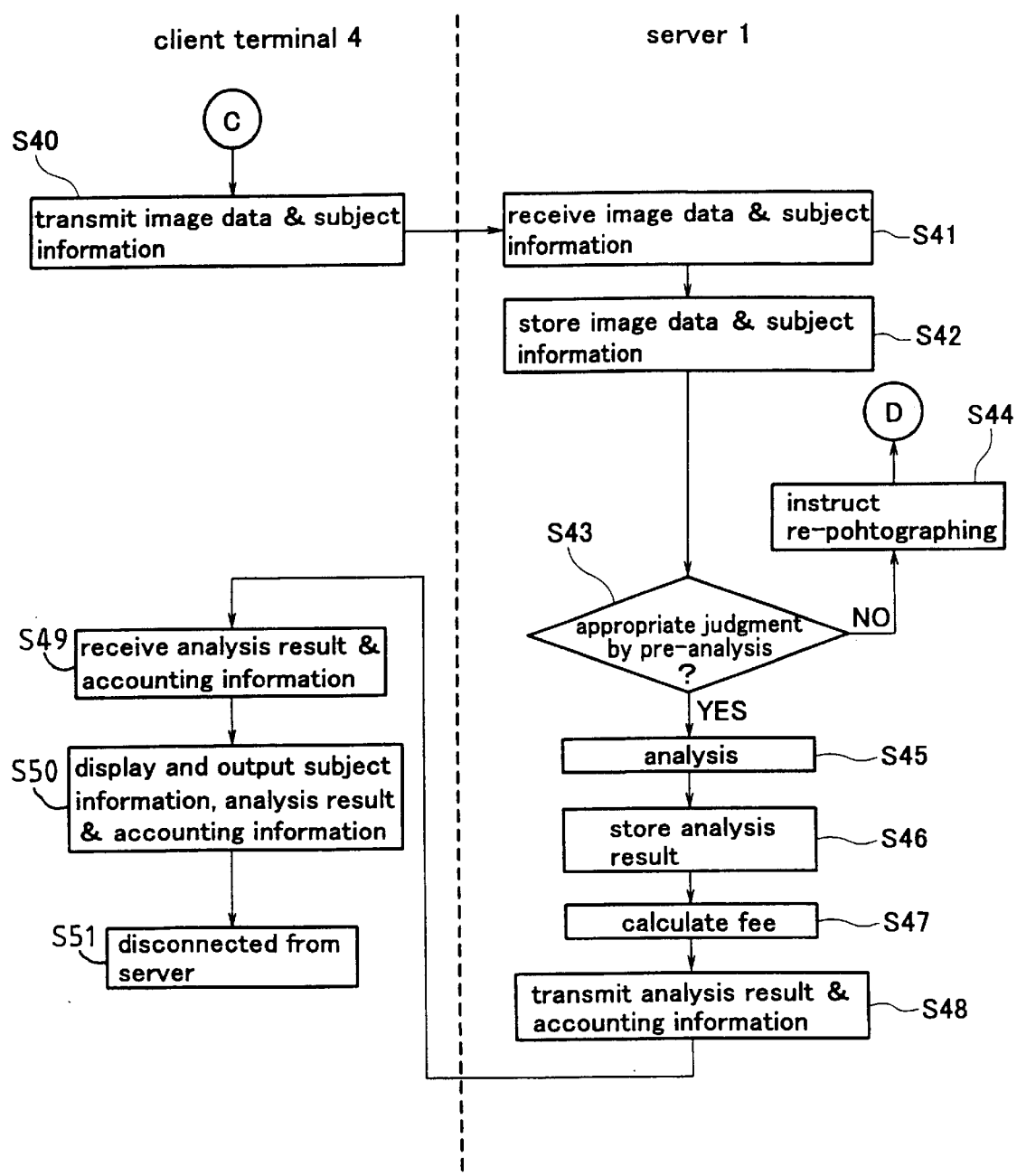
FIG. 6 is a flowchart showing a procedure of the corneal endothelium analysis service system of FIG. 1 based on communication between the server and the client terminal.
Figure 10:
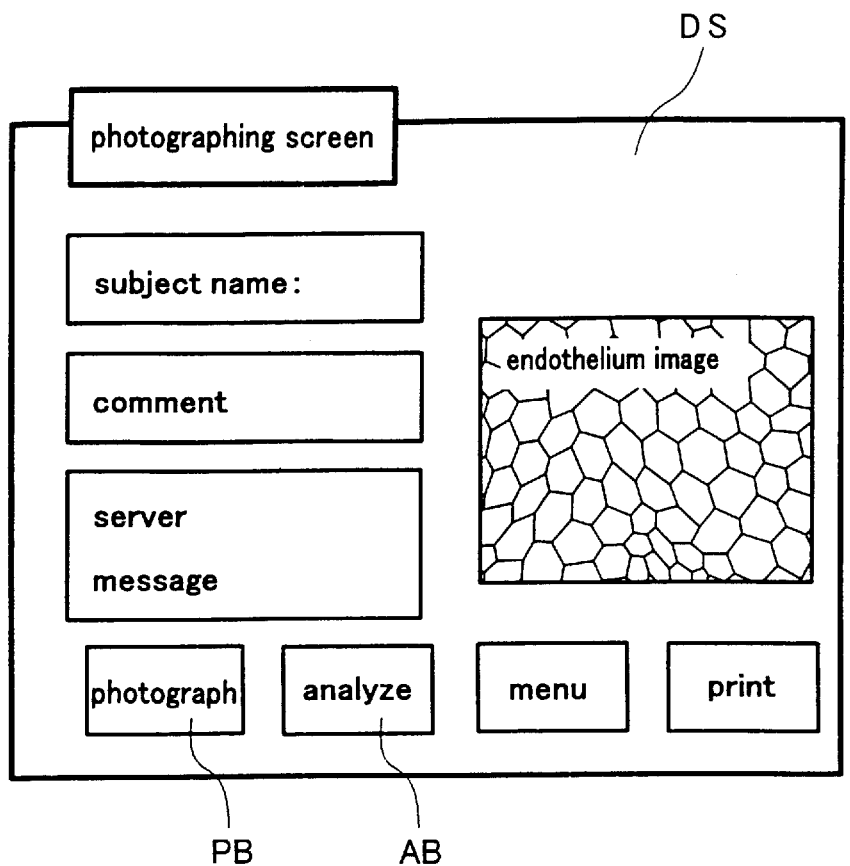
FIG. 10 is a view showing a further example of the image display of the site on Internet that executes the corneal endothelium analysis service system of FIG. 1.

On the other hand, when it is judged that the subject can be photographed in Step S16, the photographing instruction is transmitted from the server 1 to the client terminal 4 (Step S18). Automatically or by an operation of a photographing button PB on the standby screen CS by the client 3, the photographing operation of the corneal endothelium photographing device 5 is started. In the photographing operation, first, the photographing portion drive mechanism of the corneal endothelium photographing device 5 drives the photographing portion 22 to be moved in X and Y directions (Step S19). The alignment optical system confirms alignment (Step S20). Then, the photographing portion drive mechanism of the corneal endothelium photographing device 5 drives the photographing portion 22 to be moved in X, Y, and Z directions (Step S21). The alignment optical system and the focusing optical system respectively confirm alignment and focusing with accuracy (Step S22). After the alignment and focusing are confirmed, the corneal endothelium of the subject is photographed by the photographing optical system (Step S23). A photographing screen DS of FIG. 10 is displayed on the client terminal 4 and the image of the photographed corneal endothelium is displayed on the screen DS. A case where the "photographing and analysis" is selected on the menu screen BS will be described later (FIG. 6). Alternatively, without providing the control portion in the corneal endothelium photographing device 5, the information of the alignment optical system and the focusing optical system can be received by the server 1 and the photographing portion drive mechanism can be controlled by the server 1. In this case, Steps S18–S23 correspond to the photographing steps.

When the "only photographing" is selected on the menu BS (Step S24), automatically in the server 1, the calculating means calculates the fee and when the fee has been prepaid, the balance of the client 3 is calculated (calculating step S25). Then, the accounting information and the subject information are transmitted to the client terminal 4 (accounting step S26). At the client terminal 4, the accounting information and the subject information are displayed on the photographing screen DS as the server message in addition to the corneal endothelium image (Step S27). The client 3 can print out this information.

When re-photographing is desired, the standby screen CS is re-displayed on the client terminal 4 by pressing the photographing button PB on the photographing screen DS, and the above-described activation is repeated. If the corneal endothelium photographing device 5 is provided with a plurality of fixation target lamps (not shown) placed at predetermined positions and corneal photographing portion selection buttons associated with the respective fixation target lamps are provided on the photographing screen DS, then a different portion of the corneal endothelium can be photographed by selecting the corresponding button in each photographing.

When the "only photographing" is selected on the menu screen BS, the operation is ended herein. At this time, by pressing an analysis button AB on the photographing screen DS of FIG. 10, the analysis can be also selected.

When the "data retrieval" is selected on the menu screen BS (FIG. 8), the standby screen CS of FIG. 9 is displayed at the client terminal 4. As described above with reference to FIG. 7, the client 3 enters the subject information such as the subject name with which the subject can be identified (Step S30). It is confirmed whether or not the client terminal 4 has the database relating to the analysis information of the subject (Step S31), and when it is confirmed that the client terminal 4 has the database relating to the analysis information of the subject, the analysis result is retrieved therefrom for each subject (Step S32). On the other hand, when the client terminal 4 does not have the database relating to the analysis information of the subject or the terminal 4 has the database but the analysis information of the subject is not found in the database, the request for permission to use the analysis information database 16 is automatically transmitted to the server 1 (Step S33). The server 1 receives this request (Step S34), and retrieves data from the analysis information database 16 (Step S35). Then, the server 1 transmits the analysis results of the subject to the client terminal 4 (second transmission step S37). Prior to this transmission, the calculating means calculates the fee of the data retrieval (calculating step S36), and transmits the accounting information together with the retrieved data to the client terminal 4 (accounting step S37). Thereafter, the retrieved subject analysis information, the accounting information or the like are displayed at the client terminal 4 (Step S38), whereby the terminal 4 is disconnected from the server 1 (step S39). As a display screen, the photographing screen DS, the analysis screen ES or the like, may be employed. The client 3 can print out these information.

Figure 3:
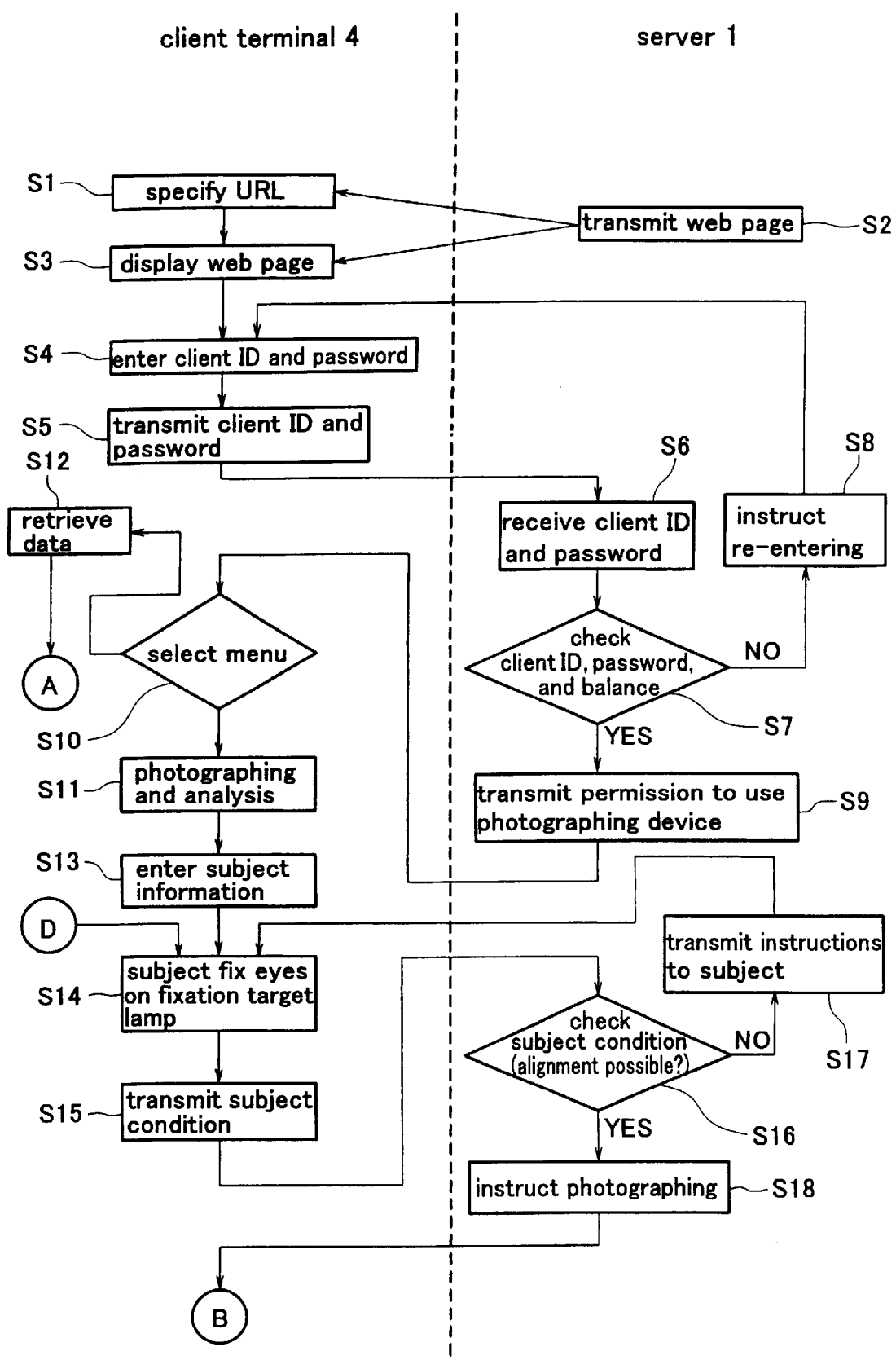
FIG. 3 is a flowchart showing a procedure of the corneal endothelium analysis service system of FIG. 1 based on communication between a server and a client terminal.
Figure 4:
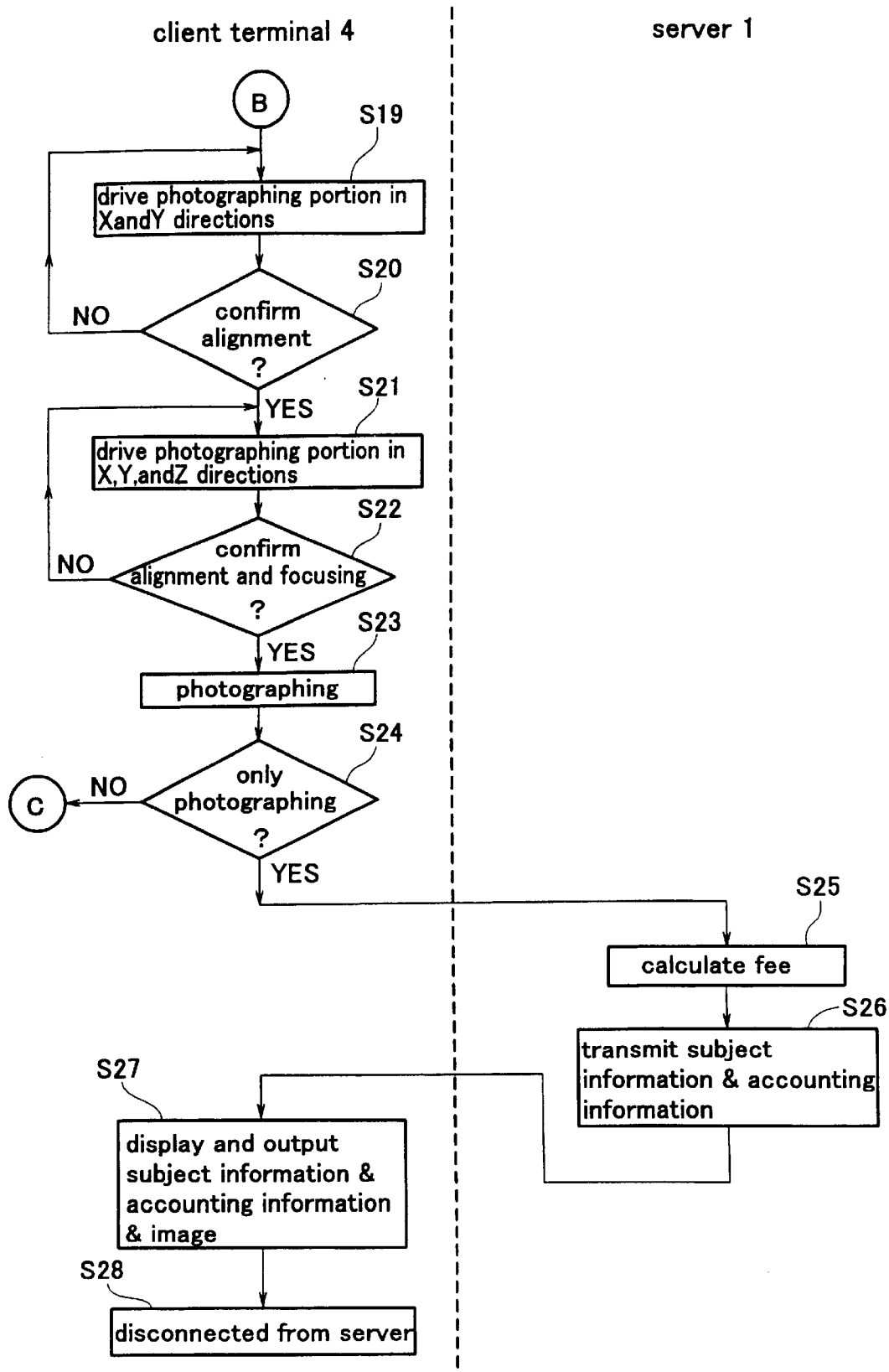
FIG. 4 is a flowchart showing a procedure of the corneal endothelium analysis service system of FIG. 1 based on communication between the server and the client terminal.
Figure 5:
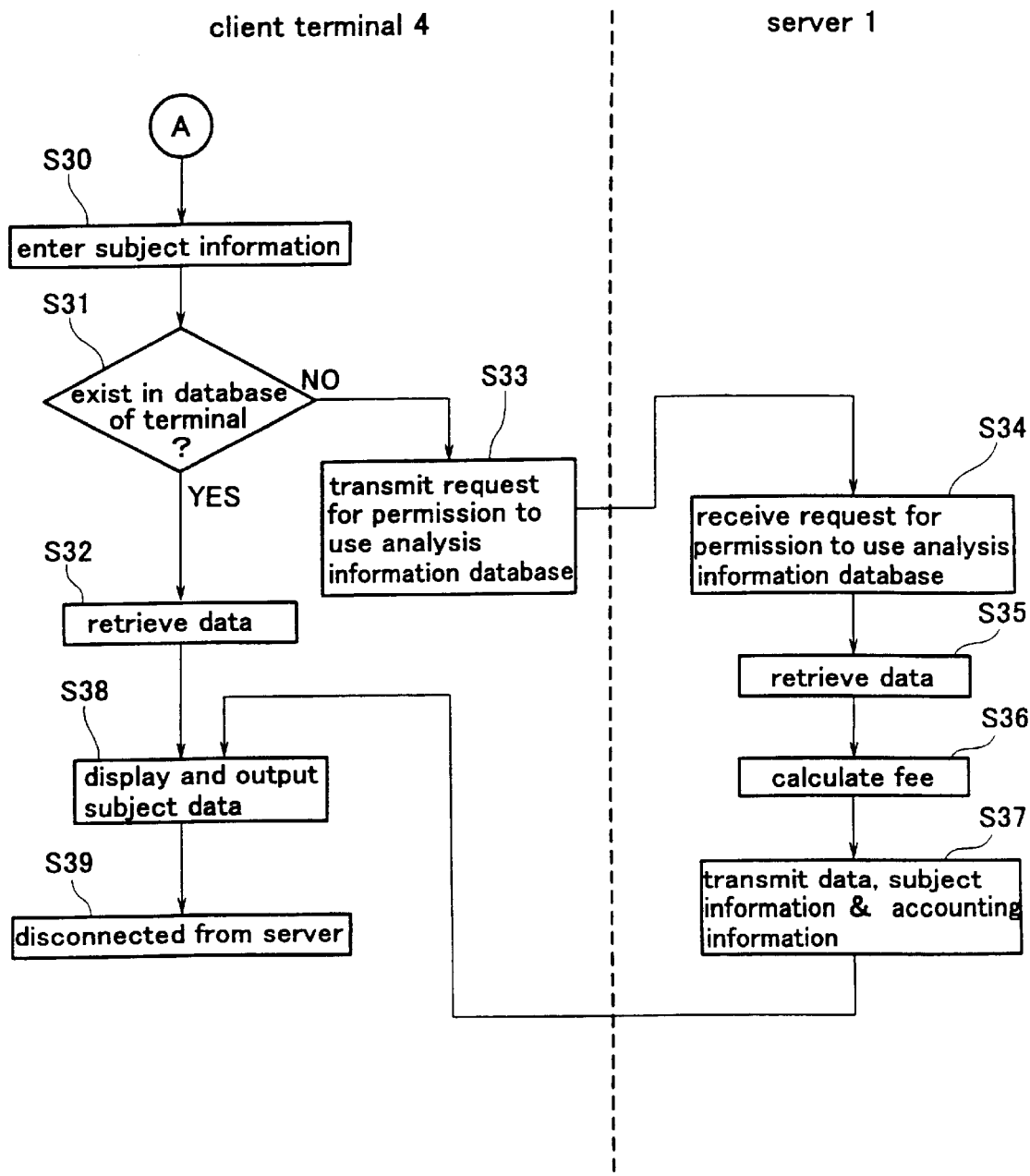
FIG. 5 is a flowchart showing a procedure of the corneal endothelium analysis service system of FIG. 1 based on communication between the server and the client terminal.

When the photographing and analysis is selected on the menu screen BS (FIG. 8), an operation is performed according to the flows of FIGS. 3, 4. When the photographing of FIG. 4 is ended, the processing goes to the flow of FIG. 6. Specifically, the image data (image data of the photographed anterior segment and corneal endothelium) and the subject information are transmitted from the client terminal 4 (Step S40), and received by the server 1 (receiving step S41). At the server 1, the received image data and subject information are stored in the image database 17 (Step S42), and it is pre-judged whether or not these images can be analyzed (Step S43). When it is judged that these images cannot be analyzed, an instruction for re-photographing is transmitted to the client terminal 4 (Step S44). On the other hand, when it is judged that the images can be analyzed, the analyzing means starts analysis (analyzing step S45) and a message stating "the images are being analyzed" or the like is transmitted to the client terminal 4.

In the analysis, general image processing is employed. Specifically, geometric image analysis such as smoothing, shading compensation, floating binalization, thinning, and do noise reducing is performed to extract a line imaging of the cell. Then, the processed corneal endothelium image, the minimum cell area of the corneal endothelium, the maximum cell area of the corneal endothelium, the average cell area of the corneal endothelium, the number of analyzed corneal endothelium cells, the number of corneal endothelium cells per unit area, standard deviation of corneal endothelium cell areas, a variation coefficient of the corneal endothelium cell areas, the rate of appearance of the hexagonal cell, and the like are calculated. When the items to be analyzed are selected by the client 3, only the items demanded by the client 3 are analyzed. The analysis results obtained in this way are stored in the analysis information database 16 as being associated with the subject (storing step S46) for data retrieval. The fee of the photographing and analysis service is calculated (calculating step S47), and the calculated accounting information, together with the analysis results, is transmitted to the client terminal 4 (first transmission step and accounting step S48).

Figure 11:
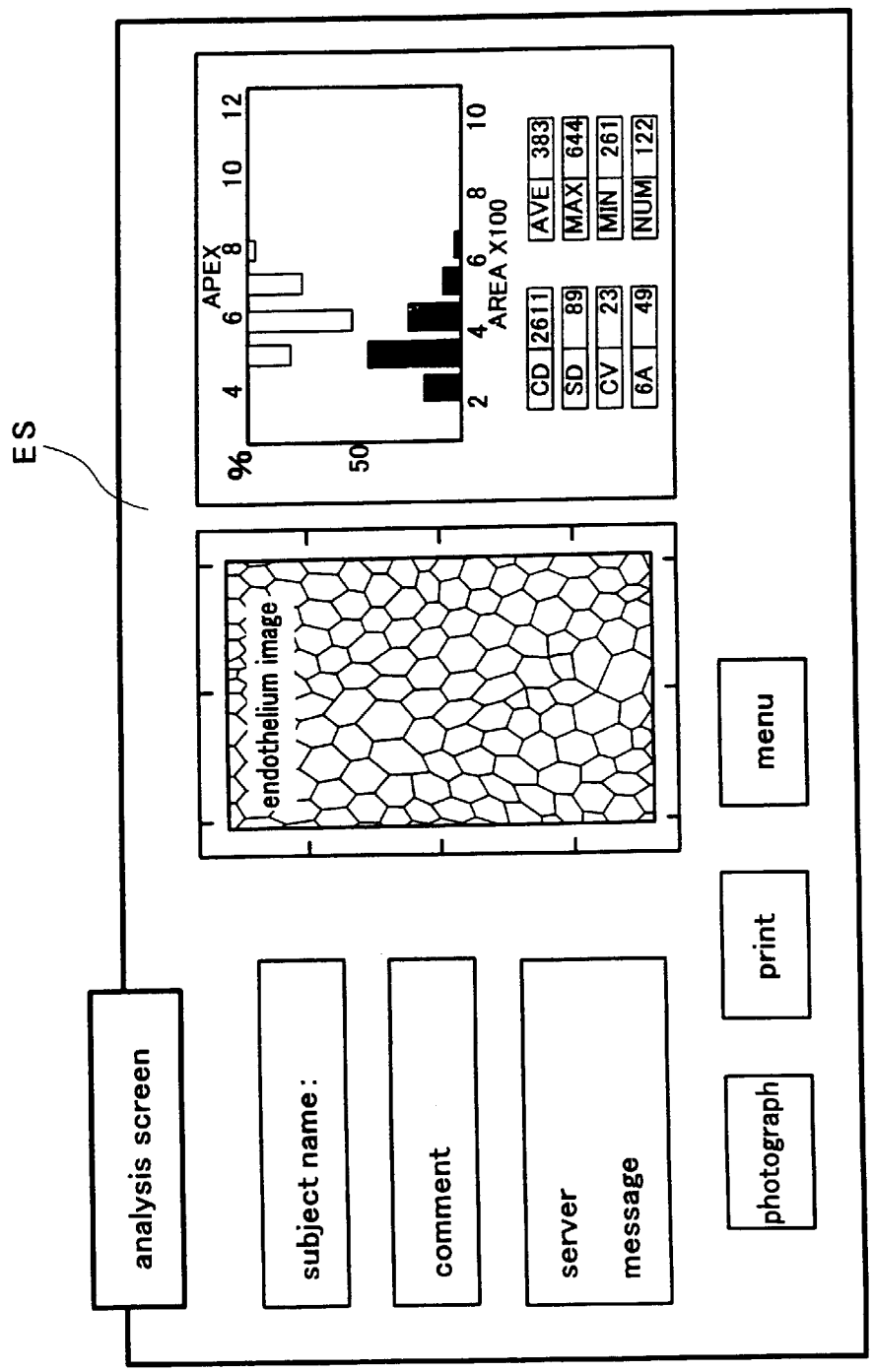
FIG. 11 is a view showing a still further example of the image display of the site on Internet that executes the corneal endothelium analysis service system of FIG. 1.

At the client terminal 4, the analysis results and the accounting information are received (Step S49). Then, an analysis screen ES is displayed as shown in FIG. 11 (Step S50). In a bar graph displayed on the analysis screen ES, upper bars indicate distribution (%) representing percentage of how many angles polygon cells have and lower bars indicate distribution of cell areas (%). CD denotes a cell density (the number of cells per 1 square millimeter). SD denotes the standard deviation of the cell areas. CV denotes the variation coefficient (standard deviation/average cell area×100). GA denotes the rate (%) of appearance of the hexagon cell. AVE denotes the average cell area (square meter). MAX denotes the maximum cell area (square meter) and MIN denotes the minimum cell area (square meter). NUM denotes the number of analyzed cells. The client 3 can print out the information (including the cell image) on the client terminal 4 as necessary (S50).

The corneal endothelium analysis service method and system of the present invention are not limited to the above embodiment. For example, the program for executing the analyzing steps or the like may be downloaded to the client terminal 4 connected to the server 1 and executed under control of the client terminal 4.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within meters and bounds of the claims, or equivalence of such meters and bounds thereof are therefore intended to be embodied by the claims.

What is claimed is:

1. A corneal endothelium analysis service method which provides an analysis service of corneal endothelium image data to a client through a network, comprising:

a receiving step for receiving the corneal endothelium image data including items demanded by the client which is transmitted from a terminal owned by the client;

an analyzing step for analyzing only the items demanded by the client that are received in the receiving step, wherein the items analyzed in the analyzing step include at least one item selected from a group comprising a processed corneal endothelium image, a minimum cell area of the corneal endothelium, a maximum cell area of the corneal endothelium, the number of analyzed corneal endothelium cells, an average cell area of the corneal endothelium, the number of corneal endothelium cells per unit area, standard deviation of corneal endothelium cell areas, a variation coefficient of the corneal endothelium cell areas and a rate of appearance of a hexagonal cell; and a first transmission step for transmitting an analysis result to the terminal.

2. The corneal endothelium analysis service method according to claim 1, further comprising:

a storing step for storing analysis results and the image data as being associated with a subject; and a second transmission step for transmitting the stored analysis results in reply to a request from the client.

3. The corneal endothelium analysis service method according to claim 1, further comprising:

a photographing step for controlling a photographing operation of a corneal endothelium photographing device owned by the client and photographing the corneal endothelium of a subject via the network and the terminal.

4. The corneal endothelium analysis service method according to claim 3, further comprising:

an instructing step for observing a condition of the subject with respect to the corneal endothelium photographing device and transmitting an instruction to the terminal to bring the subject into a condition under which the subject can be photographed via the network and the terminal.

5. The corneal endothelium analysis service method according to claim 1, further comprising:

a calculating step for calculating fee of the analysis service; and an accounting step for performing accounting of the calculated fee to the client.

6. The corneal endothelium analysis service method according to claim 1, wherein each of the steps is performed by using a site on Internet.

7. The corneal endothelium analysis service method according to claim 6, wherein each of the steps is performed under control of the terminal accessing the site.

8. A corneal endothelium analysis service system which provides an analysis service of corneal endothelium image data to a client through a network, comprising:

a receiving means for receiving the corneal endothelium image data including items demanded by the client which is transmitted from a terminal owned by the client;

an analyzing means for analyzing only the items demanded by the client that are received in the receiving means, wherein the items analyzed by the analyzing means include at least one item selected from a group comprising a processed corneal endothelium image, a minimum cell area of the corneal endothelium, a maximum cell area of the corneal endothelium the number of analyzed corneal endothelium cells, an average cell area of the corneal endothelium, the number of corneal endothelium cells per unit area, standard deviation of corneal endothelium cell areas, a variation coefficient of the corneal endothelium cell areas and a rate of appearance of a hexagonal cell; and a first transmission means for transmitting an analysis result to the terminal.

9. The corneal endothelium analysis service system according to claim 8, further comprising:

a storing means for storing analysis results and the image data as being associated with a subject; and a second transmission means for transmitting the stored analysis results in reply to a request from the client.

10. The corneal endothelium analysis service system according to claim 8, further comprising:

a photographing means for controlling a photographing operation of a corneal endothelium photographing device owned by the client and photographing the corneal endothelium of a subject via the network and the terminal.

11. The corneal endothelium analysis service system according to claim 10, further comprising:

an instructing means for observing a condition of the subject with respect to the corneal endothelium photographing device and transmitting an instruction to the terminal to bring the subject into a condition under which the subject can be photographed via the network and the terminal.

12. The corneal endothelium analysis service system according to claim 8, further comprising:

a calculating means for calculating fee of the analysis service; and an accounting means for performing accounting of the calculated fee to the client.

13. The corneal endothelium analysis service system according to claim 8, wherein each of the means is performed by using a site on Internet.

14. The corneal endothelium analysis service system according to claim 13, wherein each of the means is performed under control of the terminal accessing the site.

* * * * *

UNITED STATES PATENT AND TRADEMARK OFFICE
CERTIFICATE OF CORRECTION

PATENT NO.   : 6,659,610 B2
DATED        : December 9, 2002
INVENTOR(S)  : Tatsuya Kasahara It is certified that error appears in the above-identified patent and that said Letters Patent is hereby corrected as shown below:

<u>Column 14,</u>
Line 4, after "cell area of the corneal," please delete "endothelium" and insert
-- endothelium, -- in its place.

Signed and Sealed this

Fifteenth Day of June, 2004

JON W. DUDAS
*Acting Director of the United States Patent and Trademark Office*